(12) United States Patent
Wang et al.

(10) Patent No.: US 7,939,665 B2
(45) Date of Patent: May 10, 2011

(54) EFFICIENT PROCESS FOR THE PREPARATION OF CABERGOLINE AND ITS INTERMEDIATES

(75) Inventors: Zhi-Xian Wang, Brantford (CA); YuanQiang Li, Shanghai (CN); Murali Kondamreddy, Brantford (CA); Xiongwei Cai, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 971 days.

(21) Appl. No.: 11/797,510

(22) Filed: May 4, 2007

(65) Prior Publication Data

US 2008/0275240 A1    Nov. 6, 2008

(51) Int. Cl.
*C07D 457/04*    (2006.01)
*C07D 457/02*    (2006.01)

(52) U.S. Cl. .......................................... 546/69; 546/67
(58) Field of Classification Search .................... 546/69, 546/67
See application file for complete search history.

(56) References Cited

U.S. PATENT DOCUMENTS

| | | | |
|---|---|---|---|
| 4,166,182 | A | 8/1979 | Kornfeld et al. |
| 4,526,892 | A | 7/1985 | Salvati et al. |
| 5,382,669 | A | 1/1995 | Candiani et al. |
| 5,705,510 | A | 1/1998 | DeSantis, Jr. et al. |
| 6,696,568 | B2 | 2/2004 | Gutman et al. |

FOREIGN PATENT DOCUMENTS

| | | |
|---|---|---|
| CA | 1156648 | 11/1983 |
| CA | 2412861 | 10/2002 |
| CZ | 287 176 | 4/1999 |
| EP | 0040325 | 11/1981 |
| GB | 2103603 | 2/1983 |
| WO | WO 95/05176 | 2/1995 |
| WO | WO 99/36095 | 7/1999 |
| WO | WO 99/48484 | 9/1999 |
| WO | WO 02/085902 | 10/2002 |
| WO | WO 2006/097345 | 9/2006 |
| WO | WO2007/091039 A2 * | 8/2007 |

OTHER PUBLICATIONS

Carlsen, et al.; A greatly improved procedure for ruthenium tetraoxide catalyzed oxidations of organic compounds.; J. of Organic Chemistry; 1981;46:3936-3938.
Brambilla, et al.; Synthesis and nidation inhibitory activity of a new class of ergoline derivatives.; European J. of Medicinal Chemistry; 1989;24:421-426.
Russo, et al.; Mild, efficient trimethylaluminum-mediated cyclopropanations . . . acid.; J. Org. Chem. 1993:3589-3590.
Davis, et al.; Selective oxidation of monosaccharide derivatives to uronic acids.; Tetrahedron Lett.; 1993;34(7):1181-1184.
Mickel, et al.; Large-scale synthesis of the anti-cancer . . . fragment C7-24.; Organic Process Res. and Dev.; 2004;8:113-121.
Crombie, et al.; Synthesis and configuration of (+)-6-methyloctanic acid, a degradation product of the polymyxins.; J. of the Chem. Soc.; 1950; part III:2685-2689.
Rajashekhar, et al.; Synthesis of enantiomerically pure gamma-amino-beta-hydroxybutyric acid using mallic acid as the chiral precursor.; J. Org. Chem.; 1985;50:5480-5484.
Barak, et al.; Selective oxidation of alcohols by . . . conditions.; J. Org. Chem.;1988;53:3553-3555.
Marino, et al.; Regio and stereoselectivity of the reaction between . . . prostaglandins.; J. Org. Chem.;1987;52:4898-4913.
Sznaidman, et al.; Carbohydrate cyclic ketene acetals.; J. of Org. Chem.;1995;60:3942-3943.
McCamley, et al.; Efficient n-demethylation of opiate alkaloids using a modified nonclassical Polovski reaction.; J. of Org. Chem.;2003;68:9847-9850.
Narog, et al.; Iron(II, III)-catalyzed oxidative . . . dioxygen.; J. of Molecular Catalysis;2004;Chem 212:25-33.
Braun, et al.; German article; Chemische Berichte;1909:2035-2057.
Mantegani, et al.; Synthesis of tritium and carbon . . . prolactin lowering agent.; J. of Labelled Compounds and Radiopharmaceuticals;1991:519-533.
Ashford, et al.; A practical synthesis of cabergoline.; J. of Organic Chemistry;2002;67:7147-7150.
Candiani, et al.; The ligand effect in copper(I)-catalyzed chemoselective amide carbamoylation in cabergoline synthesis.; Synthesis Letters;1995:605-606.
Chong, et al.; Nucleophilic openings of 2,3-epoxy acids and amides mediated by . . . selectivity.; J. of Organic Chemistry;1985;50:1560-1563.
Grierson; The Polonovski reaction.; Organic Reactions;1990;ch 2;39:85-295.
Greene, et al.; Protection for the amino group.; Protective Groups in Organic Synthesis;1999;ch 7:503-653.

* cited by examiner

*Primary Examiner* — Charanjit S Aulakh

(57) ABSTRACT

This invention relates to a new and efficient process for the production of dopamine agonists such as Cabergoline and the intermediates thereof.

24 Claims, No Drawings

EFFICIENT PROCESS FOR THE PREPARATION OF CABERGOLINE AND ITS INTERMEDIATES

BACKGROUND OF THE INVENTION

N-(Ergoline-8β-carbonyl)ureas have shown potent dopamine agonist properties and have been useful as anti-Parkinson drugs and as prolactin inhibitors (U.S. Pat. No. 5,382,669 and *Eur. J. Med. Chem.* 1989, v 24, 421). One of the most potent prolactin inhibitors of this class is N-3-[(dimethylamino)propyl]-N-[(ethylamino)carbonyl]-6-(2-propenyl)-ergoline-8β-carboxamide (Cabergoline, 1).

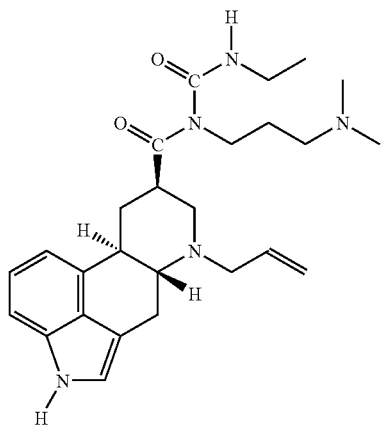

Cabergoline (1)

Cabergoline displays a significant inhibitory effect with respect to prolactin and has therapeutic properties that make it possible to treat patients who have pathological conditions associated with an abnormal prolactin level. Thus, Cabergoline is useful in human and/or veterinary medicine. The uses of Cabergoline are, for example, described in WO99/48484, WO99/36095, U.S. Pat. No. 5,705,510, WO95/05176, and EP040325. Cabergoline is particularly useful in the treatment of Parkinson's disease (PD), Restless Legs Syndrome (RLS), Progressive Supranuclear Palsy (PSP) and Multysystemic atrophy (MSA).

Cabergoline was first prepared by reaction of 6-(2-propenyl)-ergoline-8β-carboxylic acid 2 with 1-[3-(dimethylamino)propyl]-3-ethylcarbodiimide 3 in tetrahydrofuran (THF) or N,N-dimethylformamide (DMF) (U.S. Pat. No. 4,526,892, *Eur. J. Med. Chem.* 1989, v 24, 421) (Scheme 1):

Scheme 1

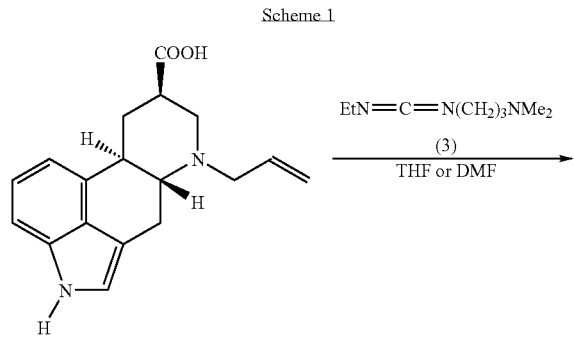

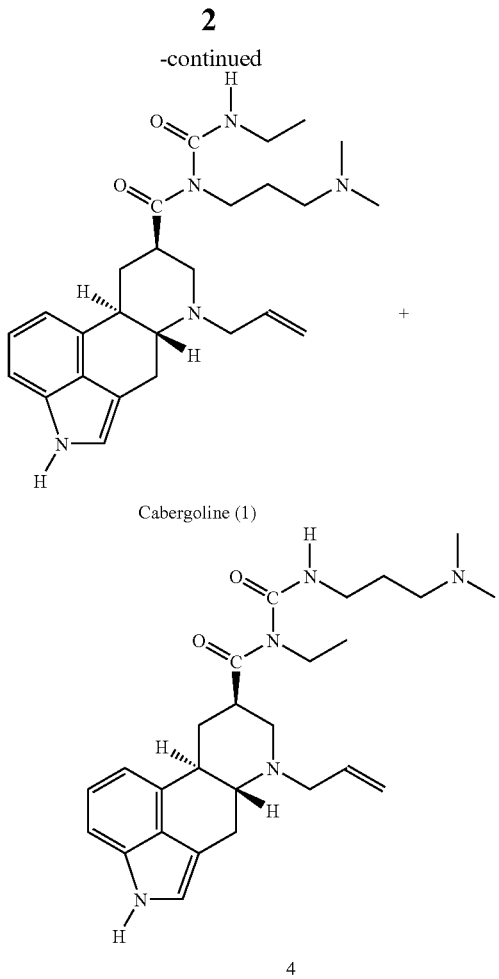

Cabergoline (1)

4

Both regioisomers 1 and 4 were obtained and the selectivity was poor (1:1 to 2:1). Therefore, the purity of the isolated Cabergoline is low as a consequence of isolation difficulties. Compounding this deficiency is the fact that there is no process to recover and recycle the undesired isomer 4.

The second method for Cabergoline preparation (*Eur. J. Med. Chem.* 1989, v 24, 421 and GB 2,103,603) was based on the direct reaction of N-[3-(dimethylamino)propyl]-6-(2-propenyl)-ergoline-8β-carboxamide with ethyl isocyanate (Scheme 2):

Scheme 2

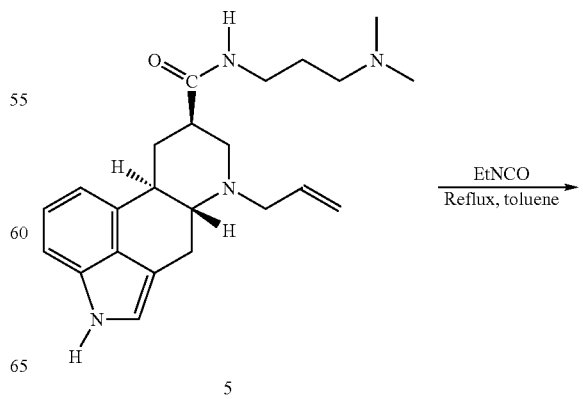

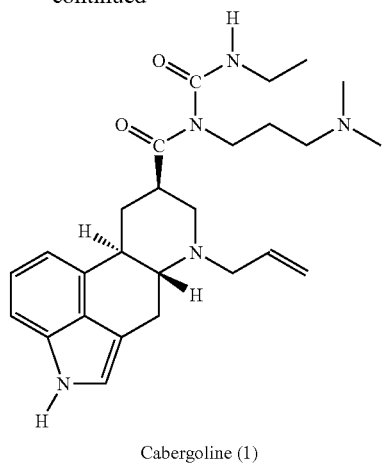

Cabergoline (1)

However, this approach uses hazardous ethyl isocyanate at elevated temperature. It requires a large excess of ethyl isocyanate (up to 40 eq.) for reasonable conversion since this reaction is controlled by the equilibrium between 5 and 1. Also, it must be conduced at 100° C. in toluene, which is 40° C. above the boiling point of ethyl isocyanate. The use of the large quantities of toxic isocyanate under drastic reaction conditions presents a major limitation for the large-scale preparation of Cabergoline by this route. In addition to the safety-related issues, conversion to Cabergoline is incomplete and competitive acylation of the indole nitrogen to give compounds 6 and 7 represents a serious side reaction that reduces yield and complicates product purification.

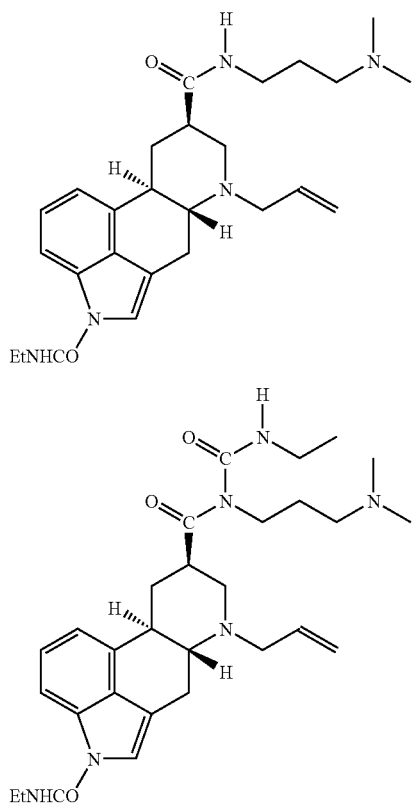

The method disclosed in U.S. Pat. No. 5,382,669 and *Syn. Lett.* 1995, 605 is based on the copper salt catalyzed reaction of ethyl isocyanate with carboxamide using phosphorous ligands. Under the optimum conditions, the reaction can be carried out at room temperature with only 3 eq. of ethyl isocyanate. However, despite these moderate reaction conditions, conversion to the product is incomplete (ca. 80%) and the product distribution and degree of conversion is similar to the uncatalyzed thermal reaction. The use of heavy metal ions in the final step of the preparation is also a drawback of this process given the tight specifications surrounding pharmaceutical actives.

WO 02/085902 disclosed a preparation of Cabergoline by silylation of carboxamide followed by treatment with ethyl isocyanate and desilylation (Scheme 3). However, this approach introduced two extra chemical steps and still employed the toxic reagent, ethyl isocyanate.

Scheme 3

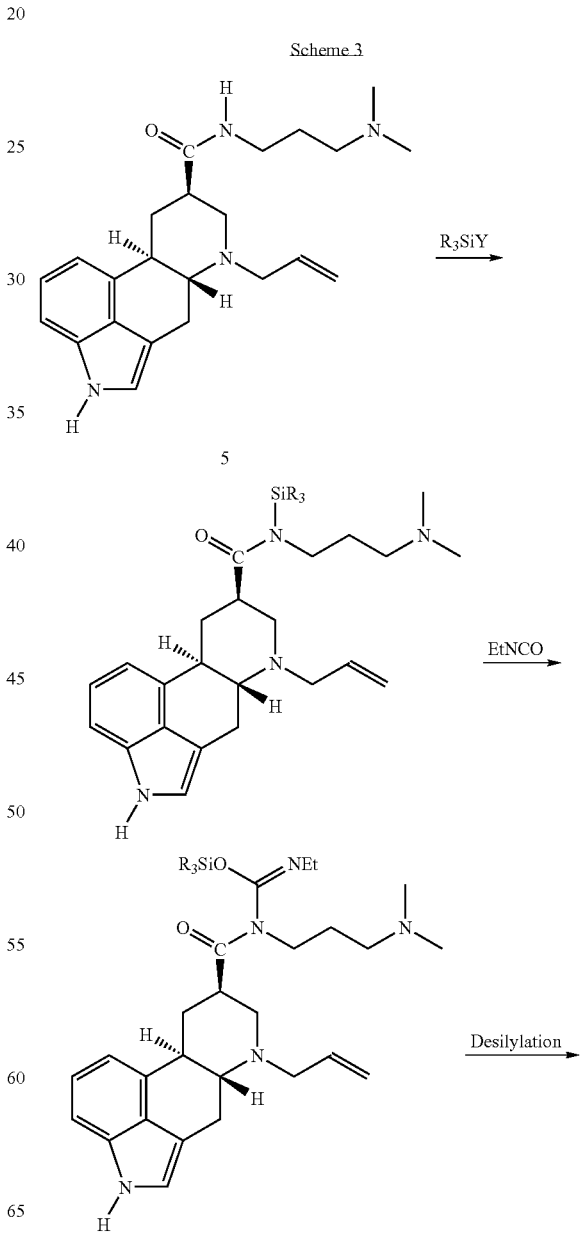

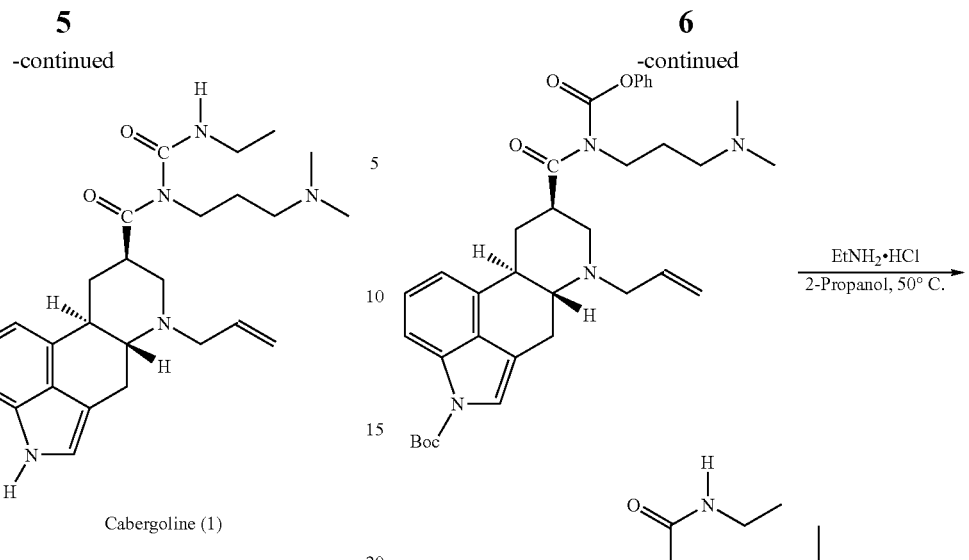

Another method for the preparation of Cabergoline (*J. Org. Chem.* 2002, v 67, 7147-7150) is described in Scheme 4. The indole nitrogen of the carboxamide is protected using a tert-butoxycarbonyl (Boc) group, and the product reacts sequentially with phenyl chloroformate and ethylamine. After removal of Boc group, Cabergoline is obtained. However, from a commercial standpoint introduction of multiple chemical steps would significantly increase process cost and the formation of impurity 9 is also a problem.

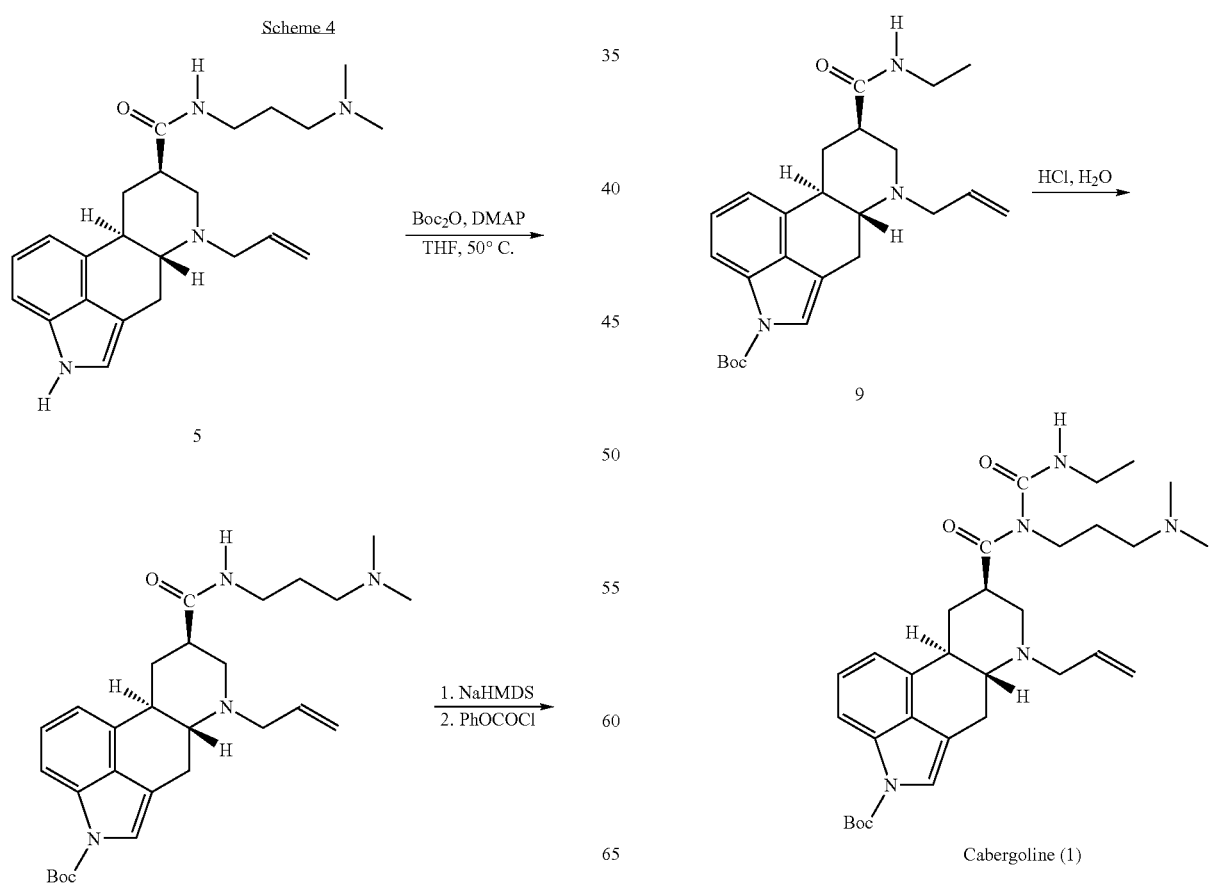

All the Cabergoline processes described above do not allow for the preparation of the advanced intermediate, 6-(2-propenyl)-ergoline-8β-carboxylic acid 2 or its derivatives. *J. Labelled Compound and Radiopharm.* 1991, v 29, 519-533, discloses the preparation of 2 from 8β-methoxycarbonylergoline, which in turn may be prepared from Lysergic acid (U.S. Pat. No. 4,166,182). However, Lysergic acid is a controlled substance and therefore has very limited availability which is obviously a severe limitation if commercial production of Cabergoline and its intermediates from this starting material was considered.

It is therefore an object of this invention to provide an efficient and cost-effective synthetic method for the preparation of Cabergoline, and intermediates thereof, from commercially non-restricted starting materials.

Further and other objects of the invention will be realized by those skilled in the art from the following summary of the invention and detailed description of embodiments of the invention.

SUMMARY OF THE INVENTION

The present invention, according to one aspect, provides a novel and efficient process for producing Cabergoline (1) using intermediates 6-(2-propenyl)-ergoline-8β-carboxylic acid 2 or its ester derivatives 19, wherein $R^2$ is selected from the group consisting of $C_1$-$C_6$ alkyl, aryl and aralkyl, from Lysergol (10) or Elymoclavine (11), which are non-controlled substances and have better commercial availability.

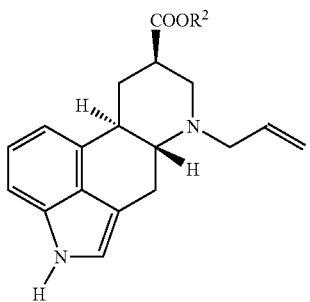

2. $R^2$ = H,
19. $R^2$ = low alkyl, aryl and aralkyl groups

In another aspect of the invention, there is provided for an improved process for producing Cabergoline 1 from 6-(2-propenyl)-ergoline-8β-carboxylic acid (2) and 1-[3-(dimethylamino)propyl]-3-ethylcarbodiimide (3) in a halogenated solvent or anisole.

This improved process significantly improves the ratio of Cabergoline 1 to the side product N-[3-(dimethylamino)propylamino]carbonyl-N-ethyl-6-(2-propenyl)-ergoline-8μ-carboxamide (4). With this improved ratio, not only does the product yield increase, but also the separation and purification procedures are simplified and the product purity is improved.

In yet another aspect of the invention there is provided for a process to recover the side product 4 by converting it into Cabergoline intermediate 2 or its ester 19 by hydrolysis or reacting with an alcohol. Compounds 2 and 19 are very expensive materials. Thus, according to an aspect of the invention, an efficient method is provided to prepare compounds 2 and 19 from compound 4, which is a major undesired side product of the Cabergoline process. Thus according to an aspect of the invention, a process according to the aspect of the invention improves overall product yield and process efficiency, and reduces production cost.

DETAILED DESCRIPTION OF ASPECTS OF THE INVENTION

According to one aspect of the invention, a process is provided for the preparation of 6-(2-propenyl)-ergoline-8β-carboxylic acid 2 or its ester derivatives 19 from Lysergol (10) or Elymoclavine (11), which are non-controlled substances and have better commercial availability.

According to another aspect of the invention this invention provides intermediate processes useful in the manufacture of 2 which may be converted to Cabergoline by known methods as desired (see Scheme 1) or by methods according to this invention.

According to another aspect of the invention, Scheme 5 outlines a preferred method for the preparation of various intermediates, for example 12 to 17, which may be used to make Cabergoline.

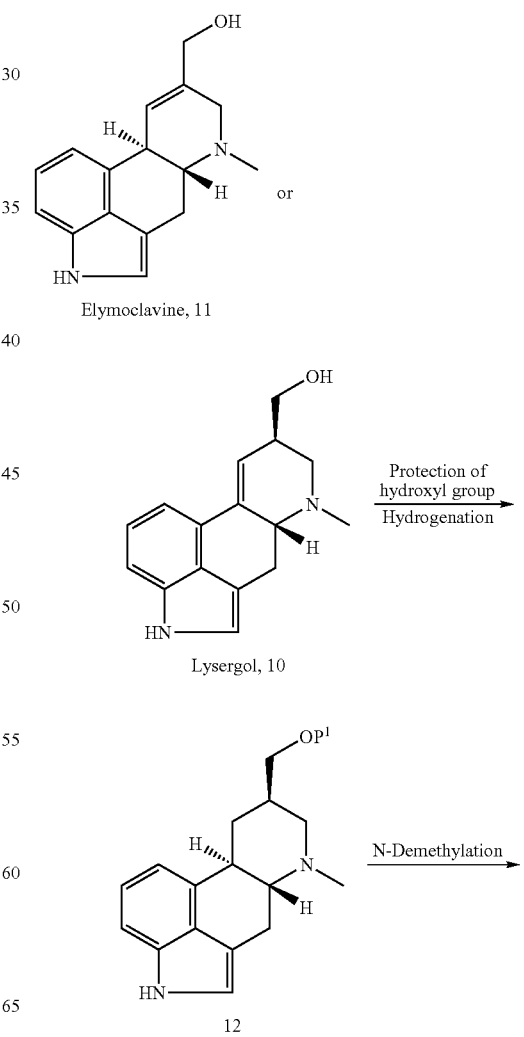

Scheme 5

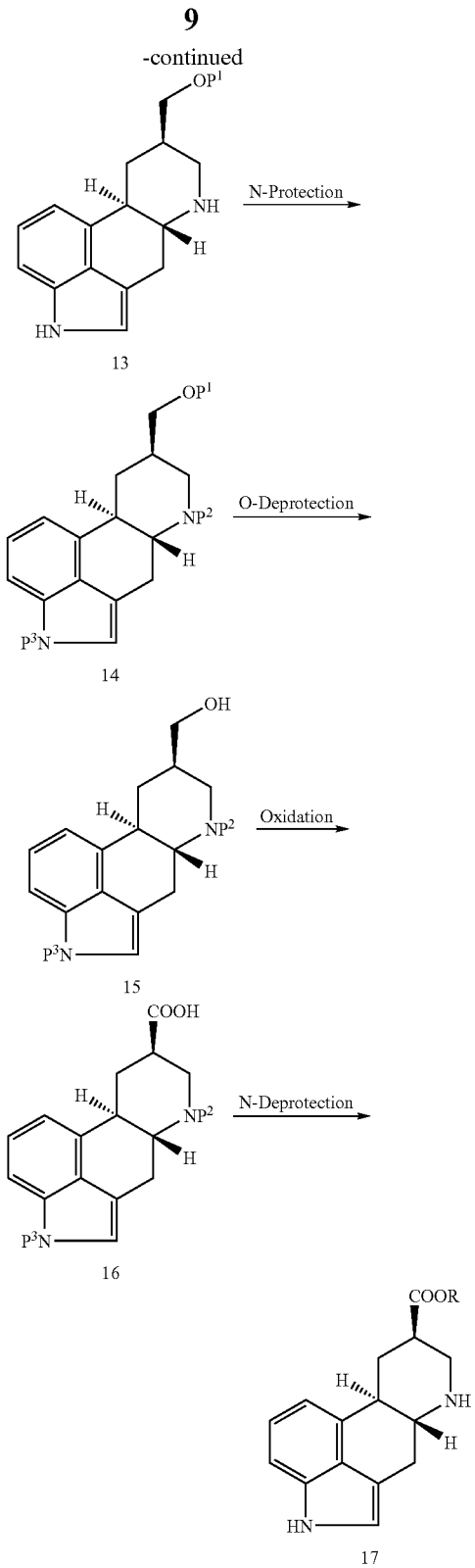

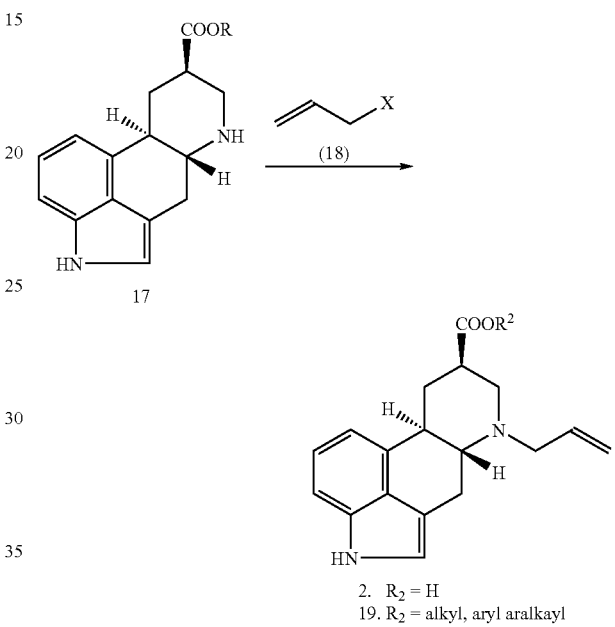

2. $R_2 = H$
19. $R_2$ = alkyl, aryl aralkayl wherein $P^1$ is a hydroxyl protecting group selected from a silyl group —$SiR^3R^4R^5$ or an acyl group —$COR^6$ wherein $R^3$, $R^4$, $R^5$ may be the same or different and are selected from the group consisting of $C_1$-$C_6$ alkyl, aryl and aralkyl groups, and $R^6$ is selected from a $C_1$-$C_6$ alkyl, aryl and aralkyl groups; $P^2$ and $P^3$ are amino protective groups and they may be the same or different, for a comprehensive review of amino protective groups, see Greene, T. W. and Wuts, P. G. M., 'Chapter 7. Protection for the amino group', in "Protective Groups in Organic Synthesis", Second Edition, John Wiley & Sons, Inc., 1999, pp 494-653, and in this context, the preferred groups are selected from $C_2$-$C_6$ acyl, aralkoxy and alkoxycarbonyl groups and silyl groups; and R selected from the group consisting of hydrogen, $C_1$-$C_6$ alkyl, aryl and aralkyl groups.

Scheme 6 outlines a preferred method utilized for the preparation of Cabergoline intermediates 2 or 19 according to an aspect of the invention:

wherein R and $R^2$ may be the same or different and are selected from the group consisting of hydrogen, $C_1$-$C_6$ alkyl, aryl and aralkyl groups; and X in compound 18 is a leaving group selected from halogens such as chloro, bromo, and iodo and sulfonate esters such as mesylate and p-tosylate.

According to another aspect of the invention, the preparation of the compound 12 from Lysergol 10 or Elymoclavine 11 may comprise protection of the hydroxyl group and reduction of carbon-carbon double bond by hydrogenation. The protection and reduction can be carried out in either order, and the product of the first reaction may be isolated or the reaction mixture can be used directly for the second reaction without isolation/purification. The protection may be carried out using general procedures described in Greene, T. W. and Wuts, P. G. M., 'Chapter 7. Protection for the amino group', in "Protective Groups in Organic Synthesis", Second Edition, John Wiley & Sons, Inc., 1999, pp 494-653. The reduction of carbon-carbon double bond by hydrogenation may be carried out in the presence of a catalyst in a solvent. The catalyst may be selected from various forms of transition metals, particularly platinum, palladium, rhodium, ruthenium, and nickel. The catalyst may be in the form of finely dispersed solids or adsorbed on inert supports such as carbon or alumina. The preferred solvent may be selected from alcohols such as methanol, ethanol, isopropanol, butanols, ethylene glycol; N,N-dialkylamides such as N,N-dimethylformamide, N,N-dimethylacetamide and 1-methyl-2-pyrrolidinone; alkyl sulfoxides and sulfones such as dimethyl sulfoxide and sulfolane and mixtures thereof. The hydrogenation may be carried out at any suitable pressure, and preferably from about 10 psi to about 200 psi. The hydrogenation temperature may range from about 0° C. to about 150° C., preferably between about 20-100° C., more preferably between about 20-70° C.

The N-demethylation may be carried out by reacting 12 with cyanogen bromide (von Braum reaction, *J. Chem. Ber.* 1909, 42, 2035), or by reacting with chloroformates, or by oxidative demethylation using the Polonovski reaction (*Organic Reactions* 1990, 39, 85-295), or by iron (II) or iron(III)-catalyzed oxidative demethylation (*J. Mol. Cat. A: Chemical,* 2004, 212, 25-33; *J. Org. Chem.* 2003, 68, 9847-9850). The preferred methods for demethylation are reactions with chloroformates. The preferred chloroformates are phenyl chloroformate, allyl chloroformate, 1-chloroethyl chloroformate, and propargyl chloroformate.

The N-protective groups $P^2$ and $P^3$ may be the same or different. However, it is preferable that $P^2$ and $P^3$ are the same. The preferred protective groups are selected from a $C_2$-$C_6$ acyl, aralkoxy and alkoxycarbonyl groups, and silyl groups, and more preferably from aralkoxy and alkoxycarbonyl groups. In a preferable reaction, compound 13 is combined with alkyloxyl or aralkoxyl chloroformate or dialkyloxyl or diaralkoxyl dicarbonate in the presence of a base or a mixture of bases in a suitable solvent or solvent mixture.

The hydroxyl protecting group $P^1$ in compound 14 can be selectively removed by general chemistry methods. For example, the ester ($P^1$=acyl group) may be removed by hydrolysis with an acid or base, and the silyl ether ($P^1$=silyl group) may be removed by reacting with a fluoride-ion source, for example, hydrogen fluoride or tetrabutylammonium fluoride.

Compound 15 can be converted into compound 16 by oxidation. The hydroxyl group in 15 may be oxidized to an aldehyde in a first reaction and then further oxidized to a carboxylic acid in a second reaction, or oxidized directly from the hydroxyl group to the carboxylic acid in one reaction. It is preferable to oxidize the hydroxyl group to the carboxylic acid group in one reaction. The oxidant may be, for example, selected from oxygen/catalyst (*J. Org. Chem.* 1995, 60, 3934; 1987, 52, 4898), hydrogen peroxide/catalyst (*J. Org. Chem.* 1988, 53, 3553), $CrO_3$ in the presence of an acid (*J. Org. Chem.* 1983, 48, 4404), metal($MnO_4$)$_n$ (*J. Chem. Soc.* 1950, 2685; *J. Org. Chem.,* 1985, 50, 5480), iodobenzene diacetate/catalyst (*Org. Proc. Res. Dev.* 2004, 8, 113), PCC, PDC, DMSO/acetic anhydride, DMSO/NCS, Dess-Martin reagent, NaOCl/catalyst (*Tetrahedron Lett.* 1993, 34, 1181, *J. Org. Chem.* 1993, 58, 3589), $NaIO_4$/catalyst (*J. Org. Chem.* 1981, 46, 3936), and $H_5IO_6$/catalyst (*J. Org. Chem.* 1985, 50, 1560). The preferable oxidant is iodobenzene diacetate/catalyst since the reaction can be done under mild condition with reduced side reactions. The suitable catalyst may be a free radical generator such as 2,2,6,6-tetramethyl-1-piperidinyloxy, free radical (TEMPO), 4-hydroxy-2,2,6,6-tetramethyl-1-piperidinyloxy, free radical (4-hydroxy-TEMPO) and 4-methoxy-2,2,6,6-tetramethyl-1-piperidinyloxy, free radical (4-MeO-TEMPO).

The amino acid protecting groups $P^2$ and $P^3$ in compound 16 can be removed by standard deprotection techniques, for example, treatment of 16 with an acid or a base, or hydrogenolysis, depending on the nature of the protecting groups. These techniques may be the methods previously described in the art, for example, techniques described in Greene, T. W. and Wuts, P. G. M., 'Chapter 7. Protection for the amino group', in "Protective Groups in Organic Synthesis", Second Edition, John Wiley & Sons, Inc., 1999, pp 494-653. Preferably, the reaction is carried out in an alcohol solvent in the presence of an acid to produce an ester product 17. Preferred acids include hydrogen chloride, sulfuric acid and thionyl chloride. Preferred alcohols include methanol, ethanol, propanol and butanol. The product 17 may be isolated as its acid addition salt form or its free base form.

The N-allylation reaction of compound 17 with 18 to provide 6-(2-propenyl)-ergoline-8β-carboxylic acid 2 or its ester derivatives 19 can be carried out in the presence of a base in a solvent. Preferred bases are selected from organic and inorganic bases, more preferably from potassium carbonate, sodium carbonate, triethylamine, diisopropylethylamine, and pyridine. Preferred solvents are selected from alkyl and aryl nitriles such as acetonitrile, propionitrile, butyronitrile, and benzonitrile; N,N-dialkylamides such as N,N-dimethylformamide, N,N-dimethylacetamide and N-methyl-2-pyrrolidinone; cyclic and acyclic alkyl sulfoxides and sulfones such as dimethyl sulfoxide and sulfolane; and halogenated hydrocarbons such as dichloromethane, dichloroethane and chlorobenzene; of which acetonitrile, propionitrile, N,N-dimethylformamide, N,N-dimethylacetamide and N-methyl-2-pyrrolidinone are preferred. When 17 is an ester, the allylation product can be isolated as an ester 19. The ester product 19 can be further hydrolyzed in the presence of a base or an acid to produce 6-(2-propenyl)ergoline-8β-carboxylic acid 2 which can be further reacted with 3 to produce Cabergoline 1 (Scheme 7):

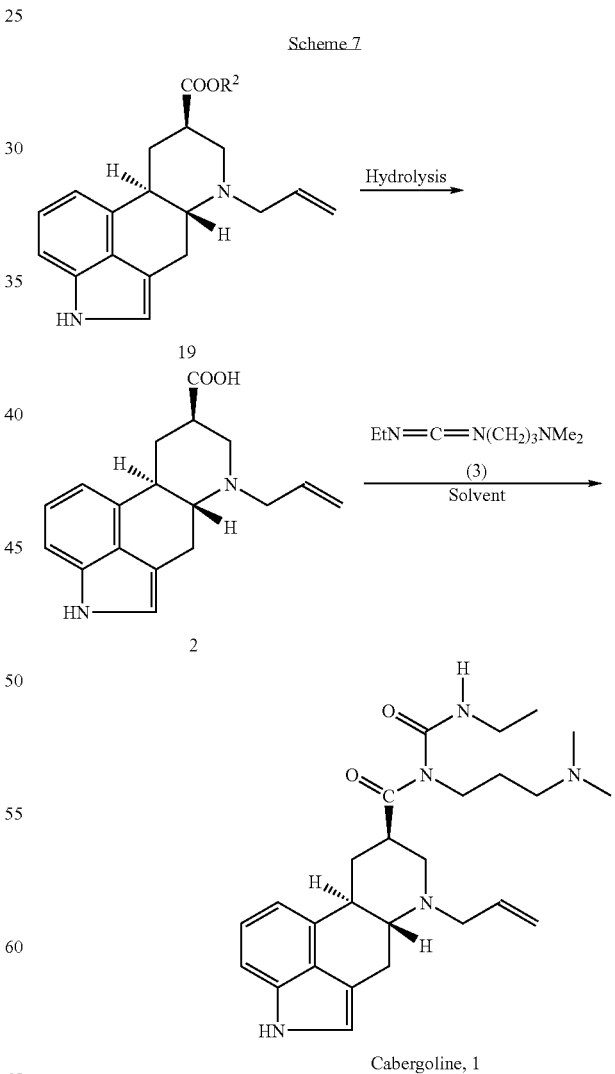

where $R^2$ is as described above.

According to another aspect of the invention, a process is provided for the preparation of Cabergoline 1 from 6-(2-propenyl)-ergoline-8μ-carboxylic acid 2 and 1-[3-(dimethylamino)propyl]-3-ethylcarbodiimide 3 in a halogenated solvent or anisole (Scheme 8):

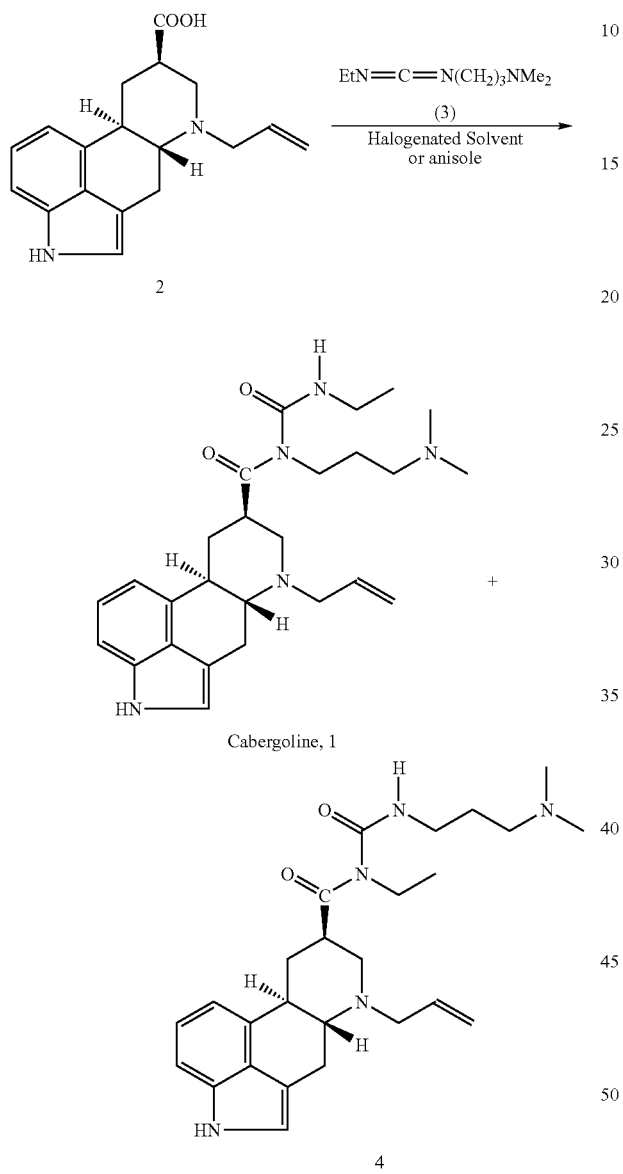

Surprisingly, we have discovered that the solvent has a dramatic effect on this reaction. The ratio of compound 1 to compound 4 is significantly improved when a halogenated solvent or anisole is used as the reaction media. The preferred halogenated solvents are selected from dichloromethane, 1,2-dichloroethane, chloroform, and chlorobenzene. The ratio can be improved to greater than 3:1, and more preferably, greater than 4:1. Compound 3 can be either in its free base form or acid addition salt form. If in its acid addition salt form, a base is added. The suitable bases can be inorganic or organic bases, preferably selected from potassium carbonate, sodium carbonate, triethylamine, diisopropylethylamine, and pyridine. The reaction temperature ranges from about 0° C. to about 100° C., preferably from about 20° C. to about 50° C.

According to yet another aspect of the invention, a process is provided to convert undesired isomer N-[3-(dimethylamino)propylamino]carbonyl-N-ethyl-6-(2-propenyl)-ergoline-8β-carboxamide 4 into 6-(2-propenyl)-ergoline-8μ-carboxylic acid 2 or its ester 19 by hydrolysis or reacting with an alcohol (Scheme 9).

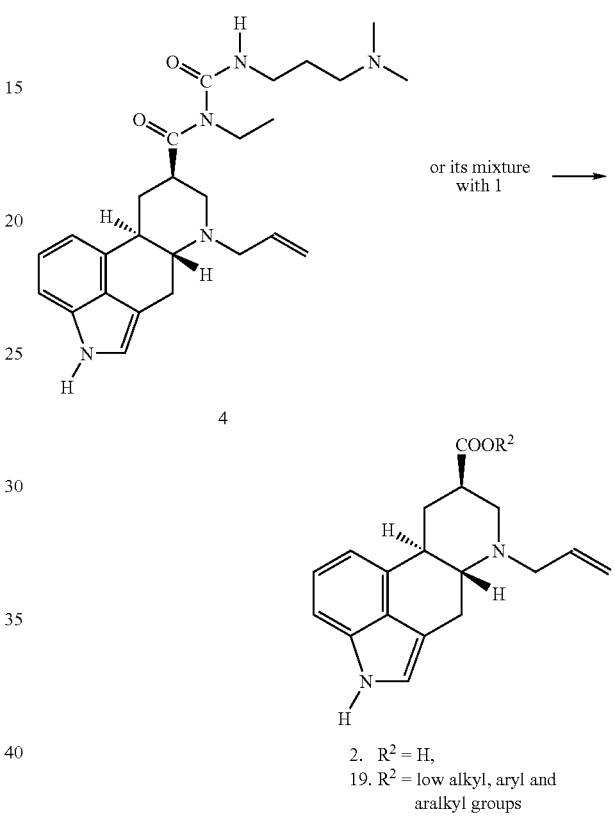

Compound 4 is a side product of the last step of Cabergoline synthesis. It is desirable to recover it and convert it into Cabergoline or a useful intermediate for Cabergoline. Surprisingly, we have found that hydrolysis of 4 or its mixture with Cabergoline gives the Cabergoline intermediate 6-(2-propenyl)-ergoline-8β-carboxylic acid 2 in high yield and good purity. Hydrolysis may be carried out in the presence of acid or base. The suitable acids are selected from hydrochloric acid, sulfuric acid, nitric acid, hydrobromic acid and the like. The suitable bases are selected from alkali metal hydroxide such as sodium hydroxide and potassium hydroxide. The reaction may be carried out in water and a water-miscible organic solvent, or in water and a water-immiscible organic solvent in the presence of a phase transfer catalyst such as quaternary ammonium salts and crown ethers. The reaction temperature ranges from about 0° C. to about 100° C., and preferably from about 0° C. to about 50° C. Cabergoline (1) may be separated and purified using chromatography or crystallization methods, and preferably a crystallization method.

Surprisingly, we have also found that compound 4 or its mixture with Cabergoline can be converted to 6-(2-propenyl)-ergoline-8β-carboxylic acid esters 19, wherein $R^2$ is selected from the group consisting of $C_1$-$C_6$ alkyl, aryl and aralkyl radicals, by reacting with an alcohol R²OH. Compound 19 is also an intermediate for the preparation of Cabergoline.

The following examples illustrate embodiments of the present invention and are not intended to be limiting.

Example 1

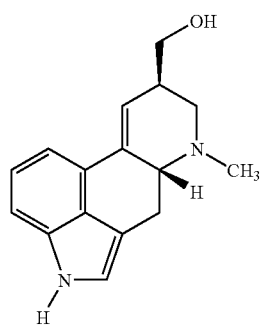

Tert-butyldimethylsilyl chloride (TBS-Cl, 19.6 g) is added into a mixture of Lysergol (30 g) and triethylamine (16.7 g) in N,N-dimethylformamide (150 mL) and the mixture is stirred at room temperature for 2-3 h. The mixture is cooled and water (240 mL) is added. The resulting suspension is stirred for an additional 2 h and then filtered and washed with water. The product is dried under vacuum to give 42 g of 8β-(tert-butyldimethylsiloxymethyl)-9,10-didehydro-6-methyl-ergoline in 96.5% yield.

Example 2

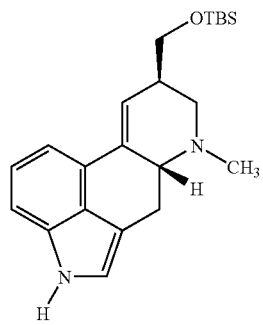

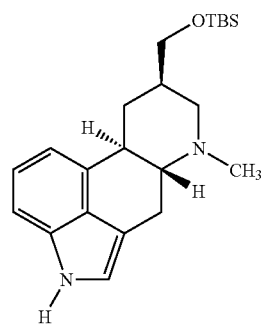

A mixture of 8β-(tert-Butyldimethylsiloxymethyl)-9,10-didehydro-6-methyl-ergoline (40 g) and Palladium on carbon (5%, 50% wet, 2.4 g) in N,N-dimethylformamide (200 mL) is hydrogenated at 60-70° C. and 40-50 psi until the theoretical volume of hydrogen has been absorbed. The mixture is allowed to cool and diluted with dichloromethane (160 mL). The reaction mixture is filtered and the insoluble material is washed with more dichloromethane. The filtrate is evaporated to about 140 mL and diluted with water (320 mL). The resulting suspension is cooled and filtered, washed with water and heptanes. The solid is dried under vacuum to give 36.3 g of 8μ-(tert-Butyldimethylsiloxymethyl)-6-methyl-ergoline in 91% yield.

Example 3

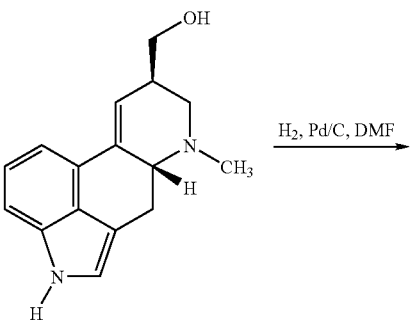

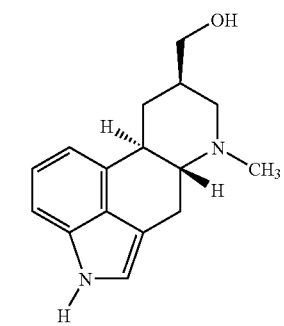

A mixture of Lysergol (1.5 g) and Palladium on carbon (5%, 50% wet, 75 mg) in N,N-dimethylformamide (15 mL) is hydrogenated at 50-60° C. and 40-50 psi until the theoretical volume of hydrogen has been absorbed. The reaction mixture is cooled, filtered and the insoluble material is washed with more N,N-dimethylformamide. The filtrate is evaporated to dryness and suspended with water. The resulting suspension is filtered, washed with more water. The solid is dried under vacuum to give 1.47 g of dihydrolysergol in 97% yield.

Example 4

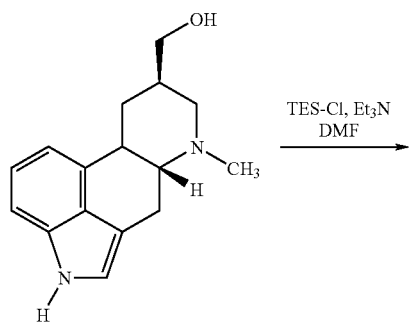

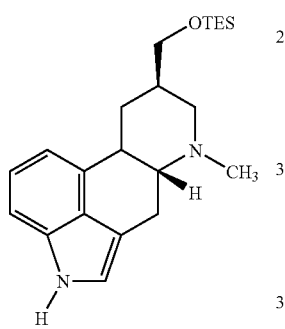

Triethylsilyl chloride (TES-Cl, 1.30 g) is added into a mixture of dihydrolysergol (1.47 g), triethylamine (1.74 g) and DMAP (0.14 g) in N,N-dimethylformamide (10 mL) and the mixture is stirred at room temperature. After complete reaction, the mixture is cooled and water (15 mL) is added. The resulted suspension is stirred for an additional 2 h and then filtered and washed with water. The product is dried and recrystallized from dichloromethane/heptanes to give 1.47 g of 8β-(trimethylsiloxymethyl)-9,10-didehydro-6-methyl-ergoline in 70% yield.

Example 5

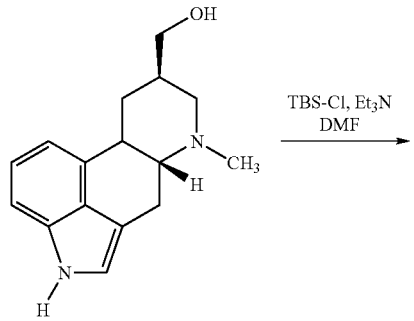

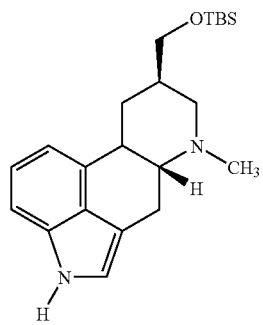

Tert-butyldimethylsilyl chloride (TBS-Cl, 0.32 g) is added into a mixture of dihydrolysergol (0.5 g), triethylamine (0.43 g) and DMAP (35 mg) in N,N-dimethylformamide (5 mL) and the mixture is stirred at room temperature. After reaction completion, the mixture is cooled and water (15 mL) is added. The resulting suspension is stirred for an additional 2 h and then filtered and washed with water. The product is dried and recrystallized from dichloromethane/heptanes to provide 0.58 g of 8β-(tert-butyldimethylsiloxymethyl)-9,10-6-methyl-ergoline in 88% yield.

Example 6

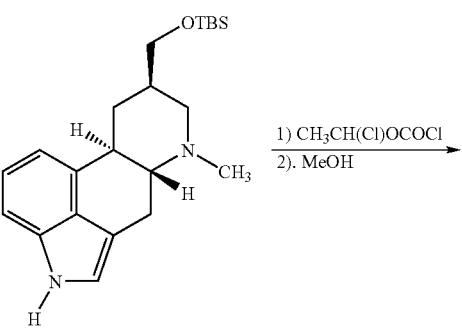

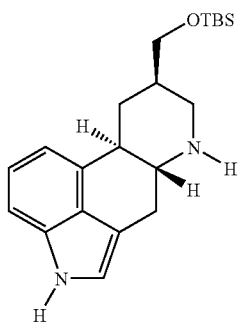

1-Chloroethyl chloroformate (164 g) is slowly added into a mixture of 8μ-(tert-butyldimethylsiloxymethyl)-6-methyl-ergoline (355 g) in dichloromethane (1.78 L) at 0-10° C. The mixture is allowed to warm to room temperature and stirred for 10-15 h. The reaction is then quenched with solid sodium bicarbonate (161 g) and 5% sodium bicarbonate solution (1

L). The mixture is filtered and the dichloromethane layer is separated and washed with water. The organic layer is evaporated under vacuum to dryness and the residue dissolved in methanol (2.2 L). The solution is evaporated to 1.6 L and then stirred at 50-60° C. for 3-4 h. The methanol is removed and the residue is crystallized from dichloromethane to give 266 g of 8β-(tert-butyldimethylsiloxymethyl)-methylergoline in 78% yield.

Example 7

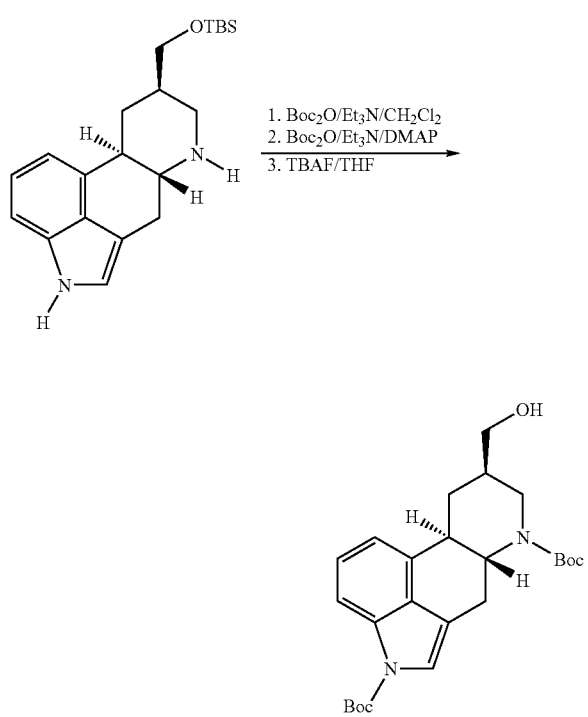

A mixture of 8β-(tert-butyldimethylsiloxymethyl)-methyl-ergoline (265 g) in dichloromethane (1.86 L) is cooled to 0-10° C. To it is slowly added triethylamine (150 g) and followed by di-tert-butyl dicarbonate (195 g). The mixture is stirred at room temperature for 4-5 h and then is washed with water. The dichloromethane layer is concentrated to about 1.3 L, and it is added triethylamine (115 g), DMAP (18.2 g) and di-tert-butyl dicarbonate (195 g). The mixture is stirred at 20-25° C. for an addition 4-5 h. The reaction mixture is washed with water and the organic layer is concentrated to about 650 mL. Tetrahydrofuran (1.1 L) is added to the residue and the solution is charged with tert-butylammonium fluoride (TBAF) (1 M solution in tetrahydrofuran) (830 mL). After stirring at room temperature for 5-6 h, the reaction mixture is concentrated under vacuum to about 530 mL and the residue is stirred with dichloromethane (1.3 L) and water (1.3 L). The aqueous layer is separated and extracted with more dichloromethane. The combined dichloromethane layers are washed with diluted acetic acid aqueous solution followed by water. The organic layer is evaporated to dryness and the residue is crystallized from acetonitrile to give 264 g of 1,6-di-(tert-butoxycarbonyl)-8μ-hydroxymethyl-ergoline in 80% yield.

Example 8

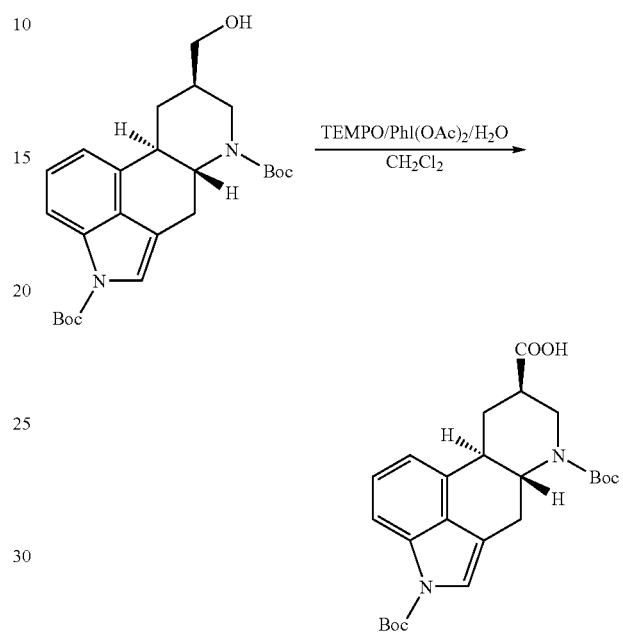

To a solution of 1,6-di-(tert-butoxycarbonyl)-8β-hydroxymethyl-ergoline (328 g) in dichloromethane (1.97 L) and water (13.5 g) is added TEMPO (22.2 g). The solution is cooled using a ice-bath and iodobenzene diacetate (597 g) is added in portions. The mixture is stirred at room temperature for 12-16 h and the reaction is monitored by TLC. The reaction is quenched with the addition of sodium thiosulfate solution (184 g in 1315 mL of water), and the organic layer is separated. The aqueous is extracted with dichloromethane (656 mL) and the combined dichloromethane layers are washed with water and then evaporated to remove the solvent. The product is crystallized from cold methanol to furnish 1,6-di-(tert-butoxycarbonyl)-ergoline-8β-carboxylic acid (334 g) in 88.5% yield.

Example 9

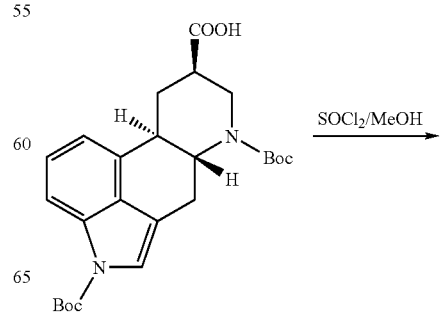

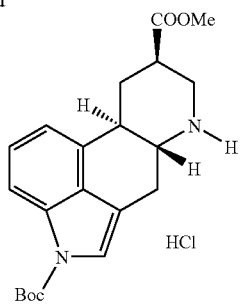

To a mixture of 1,6-di-(tert-butoxycarbonyl)-ergoline-8β-carboxylic acid (300 g) in methanol (1.2 L) is slowly added thionyl chloride (94 g). The mixture is slowly heated to 50-55° C. and stirred until reaction completion (ca. 4-5 h). The resulted suspension is cooled to room temperature and to it is added methyl t-butyl ether (600 mL) and heptanes (1.8 L). The suspension is further cooled to 0-5° C. Filtered and washed with methyl t-butyl ether. The isolated solid is dried to give methyl ergoline-8β-carboxylate hydrochloride (190.5 g) in 94.5% yield.

Example 10

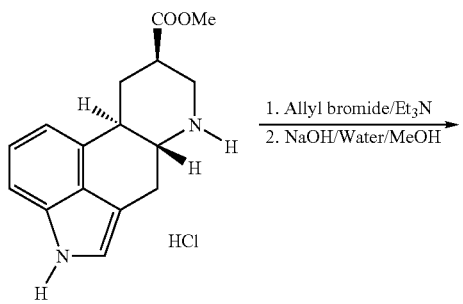

To a mixture of methyl ergoline-8μ-carboxylate hydrochloride (185 g) and triethylamine (183.3 g) in N,N-dimethylformide (555 mL) is added allyl bromide (146.3 g). The mixture is stirred at 20-30° C. for 4-5 h or until the reaction completion. The reaction mixture is then cooled to 0-5° C. and to it is added water (1.3 L) in portions. The resulting suspension is stirred at 0-5° C. for 1-3 h, then is filtered and washed with N,N-dimethylformide/water (1:2 v/v) and then water to give methyl 6-(2-propenyl)-ergoline-8β-carboxylate.

The damp product is mixed with methanol (925 mL) and to it is added 50% sodium hydroxide solution (63 g). After stirring at 20-30° C. for 2-3 h, water (500 mL) is added and the pH of the mixture is adjusted to 6-6.5 by the slow addition of hydrochloric acid. The resulting suspension is stirred at 0-5° C. for 1-2 h, then filtered, washed with water and methanol. The isolated solid is dried to give 6-(2-propenyl)-ergoline-8β-carboxylic acid (152.3 g) in 85% yield.

Example 11

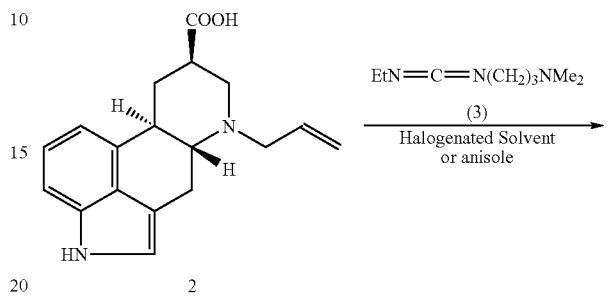

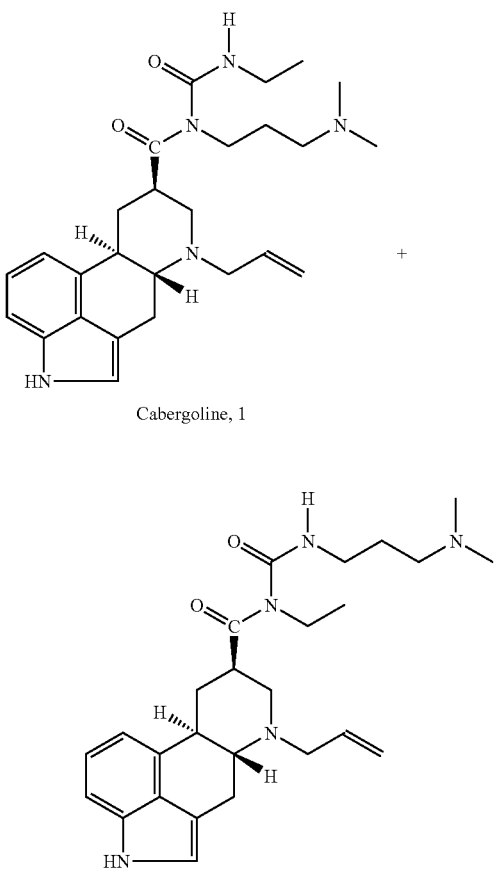

A mixture of 6-(2-propenyl)-ergoline-8β-carboxylic acid 2 (180 g), 1-[3-(dimethylamino)propyl]-3-ethylcarbodiimide hydrochloride (163.8 g) and triethylamine (92 g) in dichloromethane (1.8 L) is stirred at room temperature for 20 h. The reaction mixture is evaporated under vacuum to about 360 mL and to it is added methyl t-butyl ether and water. The ethereal layer is separated and the aqueous layer is extracted with more methyl t-butyl ether. The combined extracts are washed with water and then evaporated under vacuum to remove the solvent. HPLC showed that the ratio of Cabergoline 1 and compound 4 is about 4:1. The residue was separated by silica gel column chromatography and eluting with acetone to give Cabergoline (150 g) having more than 99% purity in 54.7% yield.

Similar experiments were carried out using other solvents and some of the results are summarized in the table below:

| Number | Solvent | Temperature (° C.) | 1:4 Ratio (HPLC) |
|---|---|---|---|
| 1 | Dichloromethane | 20-25 | 4.1:1 |
| 2 | Dichloromethane | 0-5 | 4.5:1 |
| 3 | 1,2-dichloroethane | 20-25 | 4.1:1 |
| 4 | Chlorobenzene | 20-25 | 4.7:1 |
| 5. | Ethyl acetate | 20-25 | 3.2:1 |
| 6 | Anisole | 20-25 | 4.2:1 |
| 7 | Acetonitrile | 20-25 | 2.6:1 |
| 8 | THF | 20-25 | 2.5:1 |
| 9 | DMF | 20-25 | 1.3:1 |

Example 12

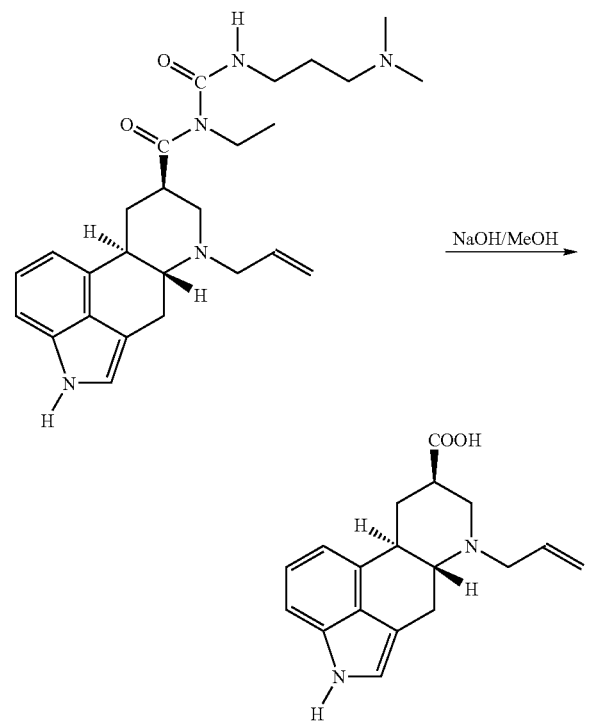

To a solution of N-[3-(dimethylamino)propylamino]carbonyl-N-ethyl-6-(2-propenyl)-ergoline-8μ-carboxamide (500 mg, 1.1 mmol) in methanol (5 mL) is added 50% sodium hydroxide solution (110 mg, 1.4 mmol). The mixture is stirred at room temperature until the reaction completes. The reaction mixture is neutralized to pH about 5-6 using 5% hydrochloric acid and diluted with 5 mL of water. The resulted suspension is filtered and rinsed with water. Dried under vacuum to give 270 mg of 6-(2-propenyl)-ergoline-8β-carboxylic acid (82% yield) as a off-white solid.

Example 13

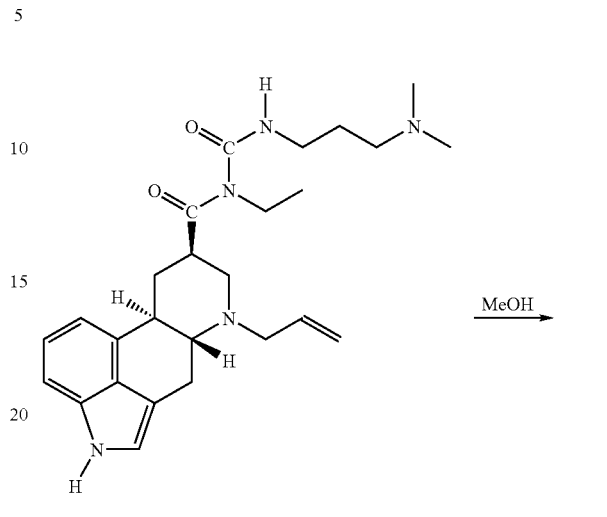

To a solution of N-[3-(dimethylamino)propylamino]carbonyl-N-ethyl-6-(2-propenyl)-ergoline-8β-carboxamide (450 mg, 1 mmol) in methanol (5 mL) is added triethylamine (110 mg, 1.1 mmol). The mixture is stirred at room temperature until the reaction completed. The reaction mixture is evaporated to remove the solvent. The residue is dissolved in methylene chloride and washed with water. The methylene chloride layer is evaporated to dryness to give 300 mg of methyl 6-(2-propenyl)-ergoline-8μ-carboxylate (96.5% yield) as a off-white solid.

As many changes can be made to the examples which exemplify the invention without departing from the scope of the invention, it is intended that all matter contained herein be considered illustrative of the invention and not in a limiting sense.

The invention claimed is:
1. A process for the preparation of Cabergoline (1)

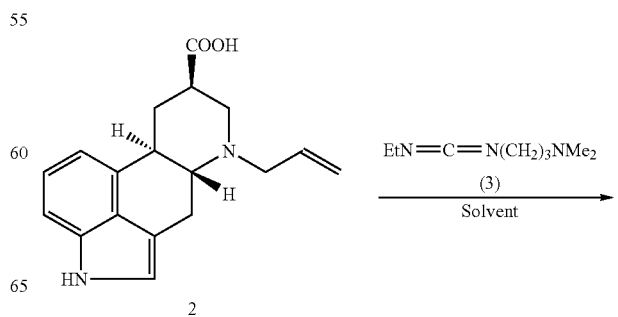

-continued

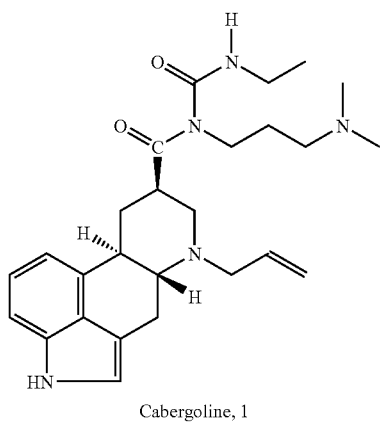
Cabergoline, 1 wherein the solvent is selected from the group consisting of halogenated solvents and anisole; and thereafter isolating Cabergoline using chromatography or crystallization.

2. The process of claim 1 wherein the halogenated solvents are selected from the group consisting of dichloromethane, 1,2-dichloroethane, chloroform, and chlorobenzene.

3. The process of claim 1 wherein compound 2 is prepared by:

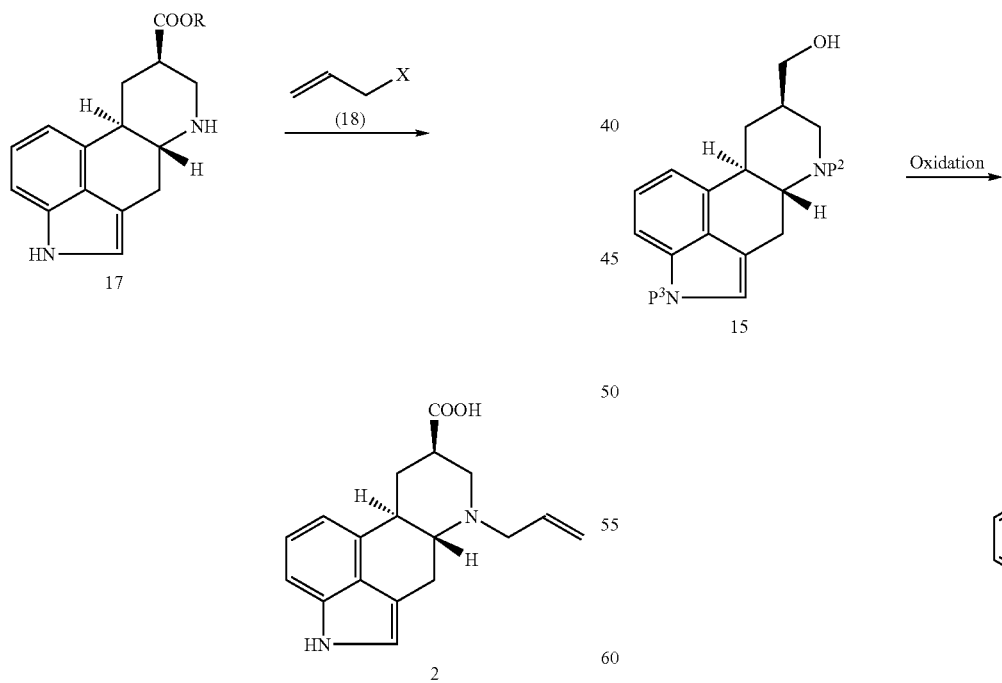

wherein X is chloro, bromo, iodo, mesylate or p-tosylate, and R is selected from the group consisting of hydrogen, $C_1$-$C_6$ alkyl, aryl and aralkyl.

4. The process of claim 3 wherein the compound of formula 17 is prepared by:

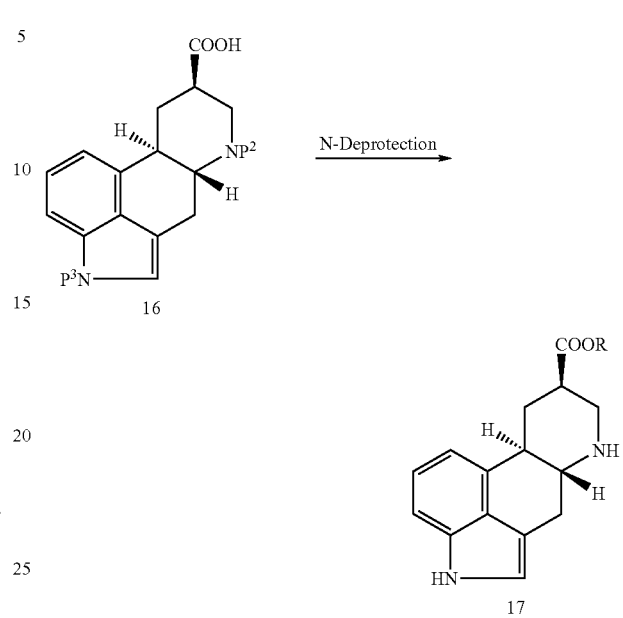

wherein $P^2$ and $P^3$ are the same or different and selected from the group consisting of $C_2$-$C_6$ acyl, aralkoxy, alkoxycarbonyl and silyl groups.

5. The process of claim 4 wherein the compound of formula 16 is prepared by:

6. The process of claim 5 wherein the oxidation is performed with iodobenzene diacetate and a catalyst selected from the group consisting of 2,2,6,6-tetramethyl-1-piperidinyloxy, 4-hydroxy-2,2,6,6-tetramethyl-1-piperidinyloxy and 4-methoxy-2,2,6,6-tetramethyl-1-piperidinyloxy.

7. The process of claim 5 wherein the compound of formula 15 is prepared by:

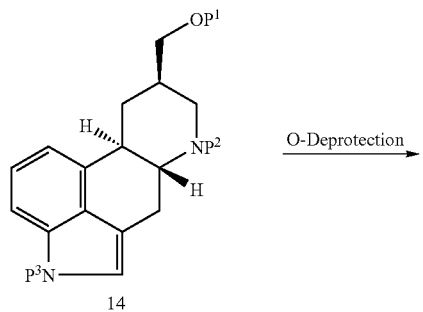

wherein $P^1$ is $SiR^3R^4R^5$ or $—COR^6$ wherein $R^3$, $R^4$ and $R^5$ are the same or different and are selected from the group consisting of $C_1$-$C_6$ alkyl, aryl, and aralkyl; and $R^6$ is selected from the group consisting of $C_1$-$C_6$ alkyl, aryl and aralkyl.

8. The process of claim 7 wherein the compound of formula 14 is prepared by:

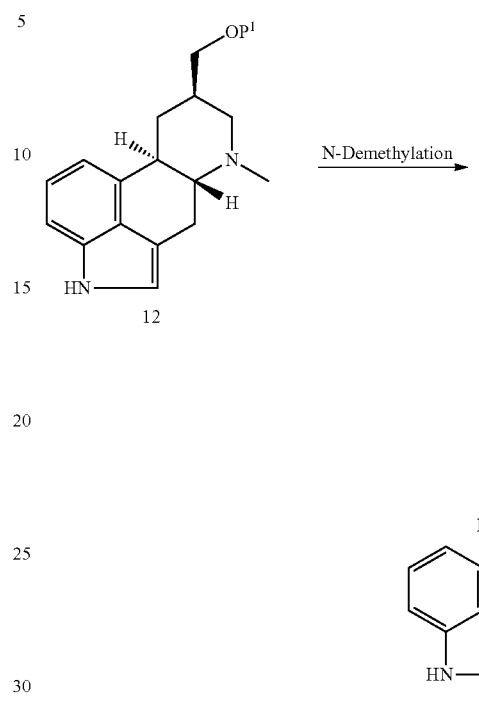

9. The process of claim 8 wherein the compound of formula 13 is prepared by:

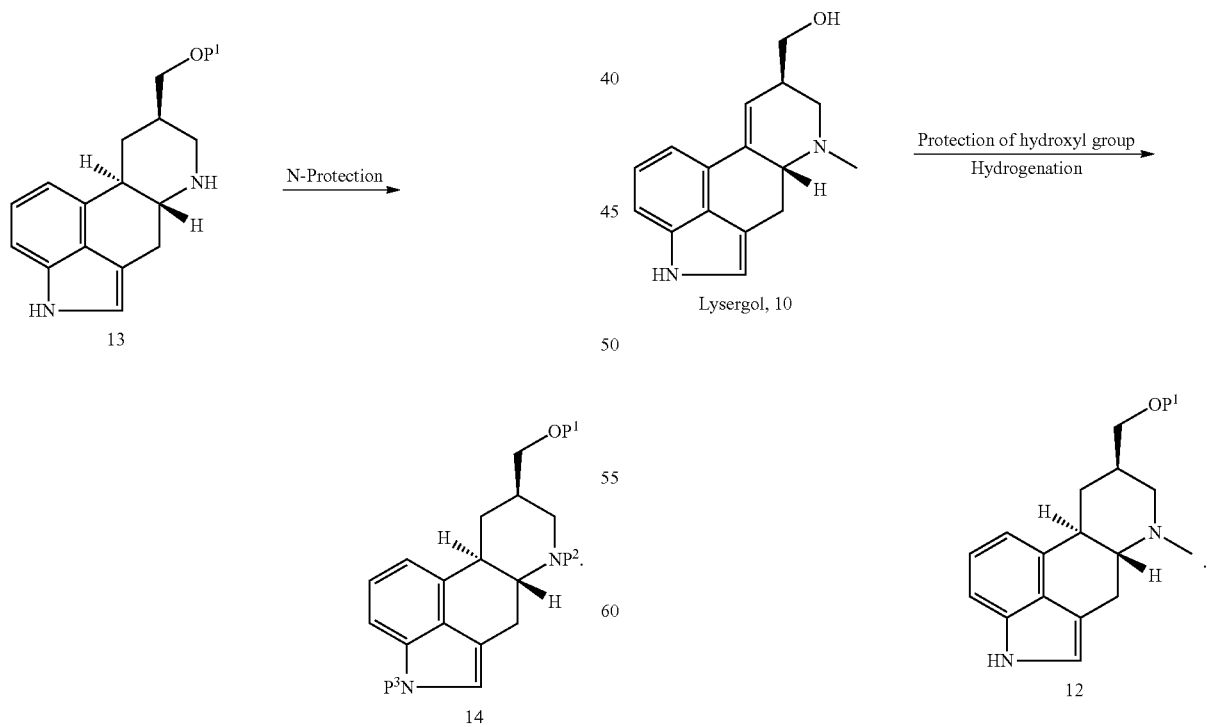

10. The process of claim 9 wherein the compound of formula 12 is prepared by:

11. The process of claim 9 wherein the compound of formula 12 is prepared by:

wherein $R^2$ is selected from the group consisting of $C_1$-$C_6$ alkyl, aryl and aralkyl; the solvent is selected from the group consisting of halogenated solvents and anisole; and thereafter isolating Cabergoline using chromatography or crystallization.

13. The process of claim 12 wherein the halogenated solvents are selected from the group consisting of dichloromethane, 1,2-dichloroethane, chloroform, and chlorobenzene.

14. The process of claim 12 wherein the compound of formula 19 is prepared by:

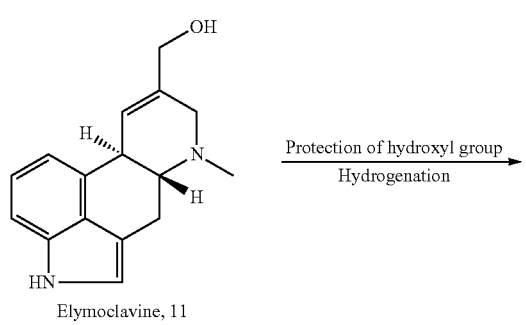

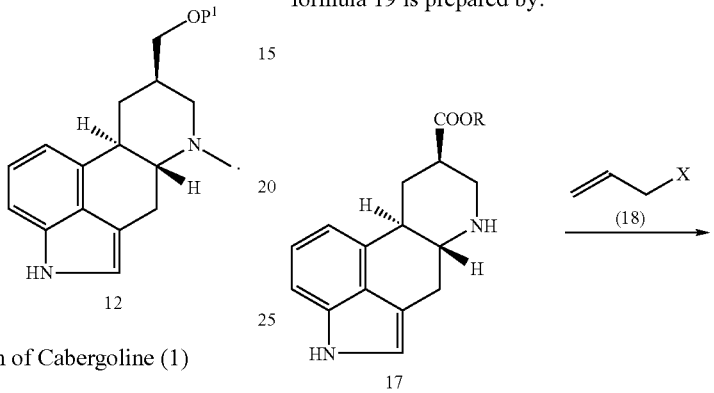

12. A process for the preparation of Cabergoline (1)

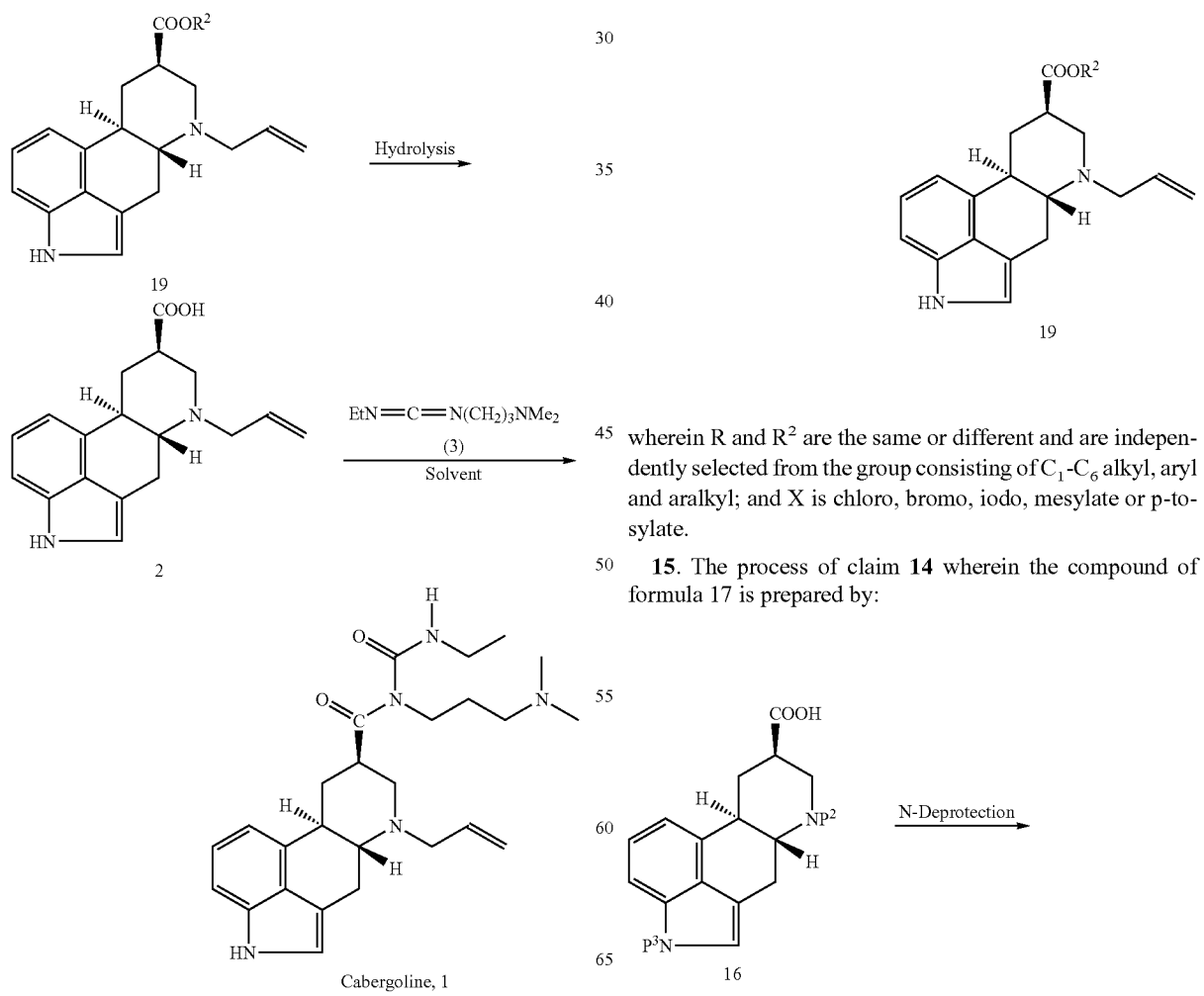

wherein R and $R^2$ are the same or different and are independently selected from the group consisting of $C_1$-$C_6$ alkyl, aryl and aralkyl; and X is chloro, bromo, iodo, mesylate or p-tosylate.

15. The process of claim 14 wherein the compound of formula 17 is prepared by:

-continued

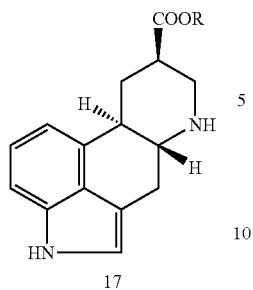

wherein P² and P³ are the same or different and selected from the group consisting of: C₂-C₆ acyl, aralkoxy, alkoxycarbonyl and silyl groups.

16. The process of claim 15 wherein the compound of formula 16 is prepared by:

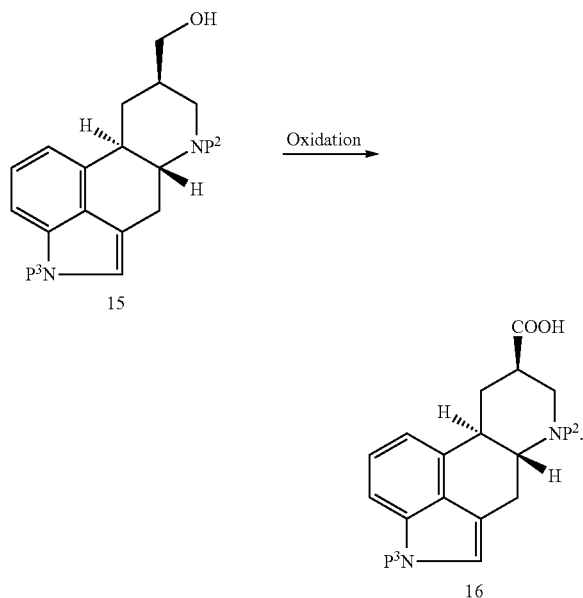

17. The process of claim 16 wherein the oxidation is performed with iodobenzene diacetate and a catalyst selected from the group consisting of 2,2,6,6-tetramethyl-1-piperidinyloxy, 4-hydroxy-2,2,6,6-tetramethyl-1-piperidinyloxy and 4-methoxy-2,2,6,6-tetramethyl-1-piperidinyloxy.

18. The process of claim 16 wherein the compound of formula 15 is prepared by:

-continued

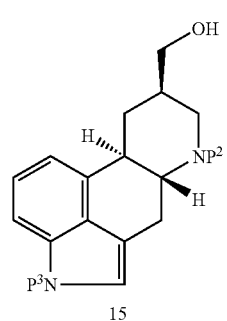

wherein P¹ is SiR³R⁴R⁵ or —COR⁶ wherein R³, R⁴ and R⁵ are the same or different and are selected from the group consisting of C₁-C₆ alkyl, aryl, and aralkyl; and R⁶ is selected from the group consisting of C₁-C₆ alkyl, aryl and aralkyl.

19. The process of claim 18 wherein the compound of formula 14 is prepared by:

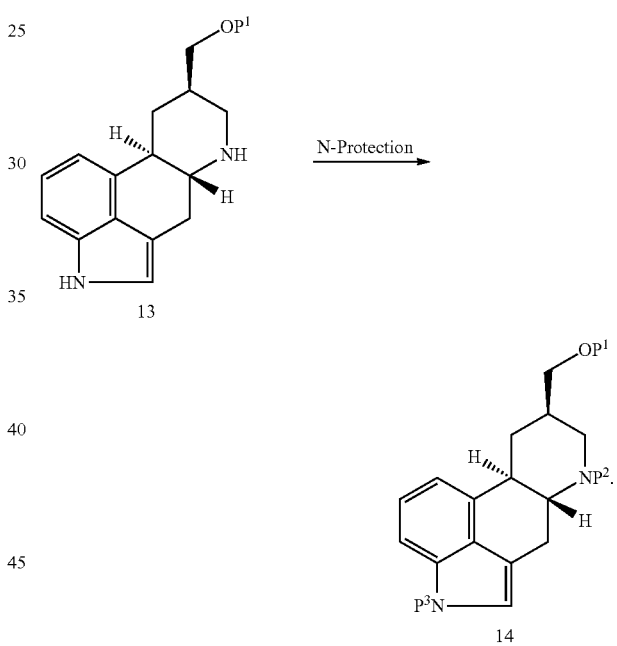

20. The process of claim 19 wherein the compound of formula 13 is prepared by:

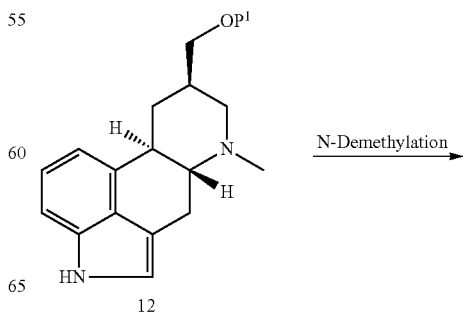

-continued

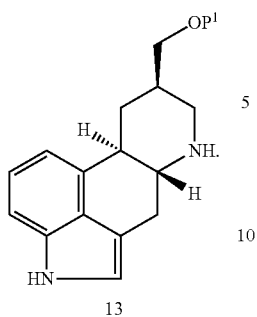

13

21. The process of claim 20 wherein the compound of formula 12 is prepared by:

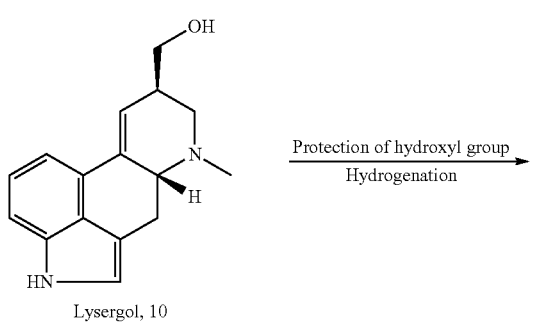

Lysergol, 10

Protection of hydroxyl group
→
Hydrogenation

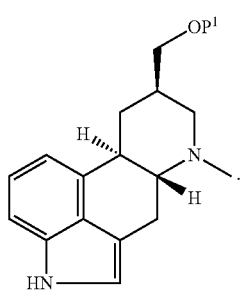

12

22. The process of claim 20 wherein 12 is prepared by:

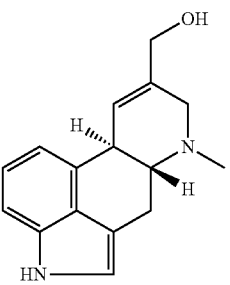

Elymoclavine, 11

Protection of hydroxyl group
→
Hydrogenation

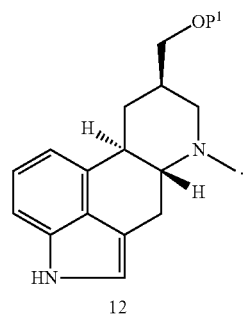

12

23. A process for the preparation of Cabergoline comprising reacting 6-(2-propenyl)-ergoline-8β-carboxylic acid (2) with 1-[3-(dimethylamino)propyl]-3-ethylcarbodiimide or its salt form in a halogenated solvent or anisole.

24. The process of claim 23, wherein the halogenated solvent is selected from the group consisting of dichloromethane, 1,2-dichloroethane, chlorobenzene, fluorobenzene and chloroform.

* * * * *